United States Patent [19]

Gevas et al.

[11] Patent Number: 5,468,494
[45] Date of Patent: Nov. 21, 1995

[54] IMMUNOGENIC COMPOSITIONS AGAINST HUMAN GASTRIN 17

[75] Inventors: Philip C. Gevas, Honolulu, Hi.; Stephen Grimes; Stephen L. Karr, both of Davis, Calif.; Dov Michaeli, Larkspur, Calif.; Robert Scibienski, Woodland, Calif.

[73] Assignee: Aphton Corp., Woodland, Calif.

[21] Appl. No.: 151,219

[22] Filed: Nov. 12, 1993

[51] Int. Cl.⁶ .................. A61K 39/385; C07K 7/06; C07K 7/08; C07K 17/06
[52] U.S. Cl. .................. 424/195.11; 424/185.1; 424/197.11; 424/198.1; 530/326; 530/329; 530/844; 514/925
[58] Field of Search .................. 424/198.1, 185.1, 424/195.11, 197.11; 530/326, 329, 844; 514/925

[56] References Cited

U.S. PATENT DOCUMENTS

| | | | |
|---|---|---|---|
| 4,069,313 | 6/1978 | Woodhour et al. | 424/209.1 |
| 4,201,770 | 5/1980 | Stevens | 424/185.1 |
| 4,384,995 | 5/1983 | Stevens | 530/404 |
| 4,526,716 | 7/1985 | Stevens | 530/403 |
| 4,691,006 | 9/1987 | Stevens | 530/324 |
| 4,894,443 | 1/1990 | Greenfield et al. | 424/179.1 |
| 5,023,077 | 6/1991 | Gevas et al. | 424/185.1 |
| 5,120,829 | 6/1992 | Pierschbacher et al. | 530/326 |
| 5,256,542 | 10/1993 | Chang | 435/7.24 |

FOREIGN PATENT DOCUMENTS

0380230  8/1990  European Pat. Off. .

OTHER PUBLICATIONS

Kothary, et al. "Identification of Progastrin-17", Biochem. Biophys. Res. Comm. 146: 884–888, 1987.
Larsson, "Characterization of Antral Gastrin Cells with Region-Specific Antiserum", J. Histochem. Cytocem. 25:1317–21, 1977.
Nemeth, J. "Development of a Sequence-Specific RIA by Using N-Terminal Gastrin 1–13 Antibody", Chem. Abs. 98: 51653w, 1983.
Dockray, G. J. "Immunochemical Studies on Big Gastrin Using NH₂-Terminal specific Antiserums", Chem. Abs. 94: 119200w, 1981.
Iwanaga, T. "Immunocytochemical Localization of the Different Gastrin Forms in the Pyloric Antrum", Biom. Res. 1:316–320, 1980.
Cunningham, et al. "High-Resolution Epitope Mapping of hGH-Receptor Interactions . . . ", Science 244:1081–1085, 1989.
Dockray, "Amino-terminal gastrin fragment in serum of Zollinger-Ellison Syndrome patients", Gatroenterology 68:222–230, 1975.
Nemeth et al. "A Gastrin Aminoterminalis 1–13 Fragmensevel Kido-Kidolgozott, . . . ", Izotoptechnika 25: 288–294, 1982.
Wendlberger, et al. "The synthesis of human big gastrin I and 32-leucine analog", Chem. Abs. 92: 198749s, 1980.
Power, et al. "A novel gastrin-processing pathway in mammalian antrum", Chem. Abs. 109: 67341z, 1988.
Dockray, et al. "Heptadecapeptide gastrin: measurement in blood by specific radioimmunoassay", Gastroenterology 71: 971–977, 1976.
Choudhury, et al. "N-terminal sequence of human big gastrin: Sequence, synthetic and immunochemical studies" Hoppe-Seyler's Z. Physiol. Chem. 361: 1719–1733, 1980.
Dockray, "Immunochemical studies on big gastrin using NH₂-terminal specific antisera", Regul. Pept. 1: 169–186, 1980.
Jones et al., Immunology Letters 24:253–260, 1990.
Flynn et al., Vet Immunol Immunopathol 31:255–266, 1992.
Archambault et al., Vet Microbiol 17(4):323–334, 1988.

Primary Examiner—Christine M. Nucker
Assistant Examiner—Julie Krsek-Staples
Attorney, Agent, or Firm—White & Case

[57] ABSTRACT

An improved immunogenic composition against human gastrin 17 comprising the peptide pGlu-Gly-Pro-Trp-Leu-Glu-Glu-Glu-Glu-Ser-Ser-Pro-Pro-Pro-Pro-Cys (SEQ ID NO.: 1) coupled to an immunogenic carrier and pharmaceutical compositions containing the same.

7 Claims, 2 Drawing Sheets

RABBIT ANTI-hG17 ANTIBODY RESPONSES TO
3 IMMUNIZATIONS WITH PEPTIDE CONJUGATES

\* #1: hG17(1-9)-Ser9--DT; #2: hG17(1-9)-Arg9--DT; #3: hG17(1-6)-Arg6--DT.
Immunizations given on days 0, 21 and 42

RABBIT ANTI-hG17 ANTIBODY RESPONSE TO ONE IMMUNIZATION WITH PEPTIDE CONJUGATE

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

Glu Gly Pro Trp Leu Glu Glu Glu Glu Ser Ser Pro Pro Pro Pro Cys
    1               5                   10                  15

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

Glu Gly Pro Trp Leu Glu Glu Glu Glu
    1               5

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal (xi) SEQUENCE DESCRIPTION: SEQ ID NO:3:

Ser Ser Pro Pro Pro Pro Cys
1               5

(2) INFORMATION FOR SEQ ID NO:4:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:4:

Glu Gly Pro Trp Leu Glu Glu Glu Glu Arg Pro Pro Pro Pro Cys
1               5                   10                  15

(2) INFORMATION FOR SEQ ID NO:5:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:5:

Arg Pro Pro Pro Pro Cys
1               5

IMMUNOGENIC COMPOSITIONS AGAINST HUMAN GASTRIN 17

BACKGROUND AND SUMMARY OF THE INVENTION

Immunization against specific disease promoting hormones may be useful in the treatment and prevention of certain diseases and cancers. Such immunological approaches to the treatment and prevention of gastric and duodenal ulcer disease and gastro-intestinal cancer are disclosed in co-assigned U.S. Pat. No. 5,023,077 and PCT application WO 90/08774. According to these immunological approaches, specific antibodies neutralize the biological activity of disease promoting gastrointestinal peptide hormones. The antibodies are specific for a particular hormone, and one or more hormones can be selectively targeted to treat a particular disease. For example, human gastrointestinal hormone gastrin 17 ("hG17") is involved in gastrointestinal disease processes including gastro-esophageal reflux disease, gastric and duodenal ulceration and cancer. Specific anti-hG17 antibodies which neutralize the action of hG17 can therefore be used to treat diseases in which hG17 is involved. The anti-hormone antibodies can be administered to the patient (i.e., passive immunization) or they can be induced in the patient by active immunization.

Active immunization against gastrointestinal peptide hormones is accomplished by administering to the patient an immunogen that contains chemical structures that induce antibodies which bind to the targeted hormone. Such chemical structures are defined as immunomimics of the targeted hormone, and can be composed of any molecule that immunologically crossreacts with the targeted hormones. Immunomimics may inherently possess the capacity to induce antibodies, e.g., they may be immunogenic, however, frequently, immunomimics are not inherently immunogenic, and they must be linked to immunogenic carrier molecules to be rendered immunogenic.

The immunogens of U.S. Pat. No. 5,023,077, the disclosure of which is hereby incorporated by reference in its entirety, and of the present invention comprise an immunogenic carder, such as diphtheria toxoid ("DT"), to which is linked peptides that are immunomimics of hG17's amino terminal epitope. The peptides are composed of two functional regions: an immunomimic and a spacer. The function of the immunomimic is to induce antibodies that bind to the targeted hormone. Any chemical structure that immunologically crossreacts with the unique amino terminal epitope of hG17 can serve as the immunomimic. In a preferred embodiment the immunomimic peptide is a fragment of hG17 which contains within it the amino terminal epitope of hG17. The spacer element of the peptide serves as a link through which the immunomimic is attached to the carder. The spacer can also affect the immune response against the immunomimic.

We have determined that certain specific peptide immunomics of hG17 coupled to a specific spacer peptide are improved immunogens which result in an unexpectedly improved immune response. One specific improved immunogen against the amino terminal epitope of hG17, comprises a peptide identified as SEQ ID NO: 1 in the Sequence Listing, of the sequence: pGlu-Gly-Pro-Trp-Leu-Glu-Glu-Glu-Glu-Ser-Ser-Pro-Pro-Pro-Pro-Cys coupled to an immunogenic carrier such as diphtheria toxoid, tetanus toxoid, keyhole limpet hemocyanin, etc. Diphtheria toxoid is the preferred immunogenic carrier in this ("hG17(1-9)-Ser9") peptide, the sequence identified as SEQ ID NO.: 2 in the Sequence Listing is pGlu-Gly-Pro-Trp-Leu-Glu-Glu-Glu-Glu- comprises the immunomimic of hG17. The remainder of the peptide's sequence, identified as SEQ ID NO.: 3 in the Sequence Listing, is Ser-Ser-Pro-Pro-Pro-Pro-Cys, constitutes the spacer.

Typically, the induction of effective antibody responses by immunization with immunomimic-carrier complexes requires two or more administrations of immunogen and takes several weeks or months for the antibody titers to rise to the desired levels. The improved immunogens of the present invention induce effective levels of antibody shortly after a single administration of immunogen.

DETAILED DESCRIPTION OF THE INVENTION

Example 1

Figure 1:
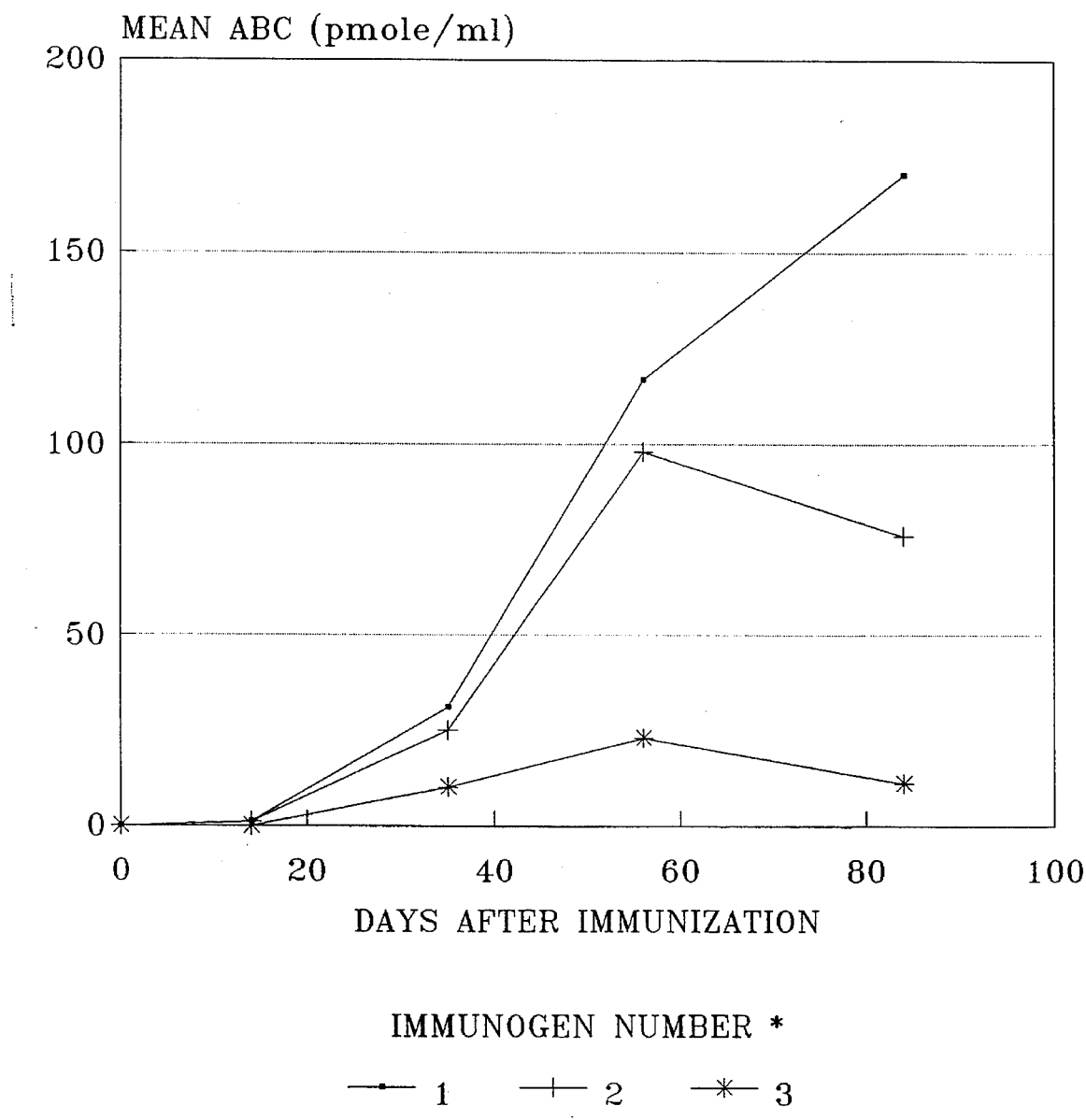
FIG. 1 depicts antibody responses in rabbits as measured by mean antibody binding capacity ("ABC") in pico moles per ml. in response to three immunizations with immunogens comprising each of the conjugates hG17(1-9)-Ser9-DT; hG17(1-9)-Arg 9-DT; and hG17(1-6)-Arg6-DT.

Peptides were prepared by standard solid state synthesis methods. Each peptide was characterized as to amino acid content and purity.

Peptides with the following amino acid sequences were synthesized:

| Peptide | Designation | Amino Acid Sequence |
| --- | --- | --- |
| 1 | hG17(1-9)-Ser9 | pGlu—Gly—Pro—Trp—Leu—Glu—Glu—Glu—Glu—Ser—Ser—Pro—Pro—Pro—Pro—Cys (SEQ ID NO.: 1) |
| 2 | hG17(1-9)-Arg9 | pGlu—Gly—Pro—Trp—Leu—Glu—Glu—Glu—Glu—Arg—Pro—Pro—Pro—Pro—Cys, identified as SEQ ID NO.: 4 in the Sequence Listing) |

Each of Peptides 1–2 contains an amino terminal immunomimic of hG17 followed by a carboxy terminal spacer. Peptide 1 comprises a 9 amino acid immunomimic of hG17 (pGlu-Gly-Pro-Trp-Leu-Glu-Glu-Glu-Glu-, SEQ ID NO.:2) followed by the "Ser" spacer (-Ser-Ser-Pro-Pro-Pro-Pro-Cys, SEQ ID NO.:3) attached to amino acid number 9 of the hG17 immunomimic. Peptide 2 comprises the 9 amino acid immunomimic (the same as in Peptide 1) followed by the "Arg" spacer (Arg-Pro-Pro-Pro-Pro-Cys, identified as SEQ ID NO.: 5 in the Sequence Listing) as described in U.S. Pat. No. 5,023,077.

Each of these peptides was conjugated to amino groups present on the Diphtheria Toxoid ("DT") immunogenic carder via the terminal peptide cysteine residue utilizing heterobifunctional linking agents containing a succinimidyl ester at one end and maleimide at the other end of the linking agent essentially as described in U.S. Pat. No. 5,023,077. To accomplish the linkage between either of the Peptides 1–2 above and the carrier, the cysteine of the peptide was first reduced. The dry peptide was dissolved in 0.1M sodium phosphate buffer, pH 8.0 with a thirty molar excess of dithiothreitol. The solution was stirred under a water saturated nitrogen gas atmosphere for four hours at room temperature. The peptide containing reduced cysteine was separated from the other components by chromatography at 4° C. over a G10 Sephadex column equilibrated with 0.2M acetic acid. The peptide was lyophilized and stored under vacuum until used.

The DT was activated by treatment with the heterobifunctional linking agent epsilon-maleimidocaproic acid N-hydroxysuccinimide ester ("EMCS"), in proportions sufficient to achieve activation of approximately 25 free amino groups per $10^5$ molecular weight of DT. In the specific instance of DT, this amounted to the addition of 6.18 mg of EMCS (purity 75%) to each 20 mg of DT.

The DT was activated by dissolving 20 mg of DT in 1 ml of 0.5M sodium phosphate buffer, pH 6.6. Separately 6.18 mg EMCS were dissolved into 0.2 ml of dimethyl formamide. Under darkened conditions, the EMCS was added dropwise in 50 microliter ("μl") amounts to the DT with stirring. After 2 hours of incubation at room temperature in darkness, the mixture was chromatographed at 4° C. on a G50 Sephadex column equilibrated with 0.1M sodium citrate buffer, pH 6.0, containing 0.1 mM ethylenediaminetetraacetic acid disodium salt ("EDTA").

Fractions containing the EMCS activated DT were pressure concentrated over a PM 10 ultrafiltration membrane under nitrogen gas in conditions of darkness. The protein content of the concentrate was determined by the BCA method (PIERCE, Ill., U.S.A.). The EMCS content of the carrier was determined by incubation of the activated DT with cysteine-HCl followed by reaction with 100 μl of 10 mM Elman's Reagent (5'5'dithio-bis (2-nitrobenzoic acid)). The optical density difference between a blank tube containing cysteine-HCl and the sample tube containing cysteine-HCl and carder was translated into 25 EMCS group content by using the molecular extinction coefficient of $13.6 \times 10^3$ for 5-thio-2-nitro-benzoic acid at 412 nm.

The reduced cysteine content ("—SH") of the peptide was also determined utilizing Elman's Reagent. Approximately 1 mg of peptide was dissolved in 1 ml of nitrogen gas saturated water and a 0.1 ml aliquot of this solution was reacted with Elman's Reagent. Utilizing the molar extinction coefficient of 5-thio-2-nitro-benzoic acid ($13.6 \times 10^3$), the free cysteine —SH was calculated.

To conjugate the reduced peptide to the activated DT, an amount of peptide containing sufficient free —SH to react with each of the EMCS activated amino groups on the DT was dissolved in 0.1M sodium citrate buffer, pH 6.0, containing 0.1 mM EDTA, and added dropwise to the EMCS activated DT under darkened conditions. After all the peptide solution had been added to the activated DT, the mixture was incubated overnight in the dark under a water saturated nitrogen gas atmosphere at room temperature.

The conjugate of the peptide linked to DT via EMCS was separated from other components of the mixture by low pressure chromatography at 4° C. over a G50 Sephadex column equilibrated with 0.2M ammonium bicarbonate. The conjugate eluted in the column void volume and was lyophilized and stored desiccated at 20° C. until used.

The conjugate may be characterized as to immunomimic peptide content by a number of methods known to those skilled in the art including weight gain, amino acid analysis, etc. Conjugates of Peptides 1–2 to DT produced by these methods were determined by amino acid analysis to have 15–28 moles of peptide per $10^5$ MW of DT and all were considered suitable as immunogens for immunization of test animals.

Example 2

The peptide-DT conjugates of Example 1 were administered in emulsions of aqueous and oily phase components that were prepared as follows. The conjugate and nor-MDP adjuvant were dissolved in phosphate buffered saline ("PBS") to produce the aqueous phase. The aqueous phase is prepared so that the concentrations of conjugate and nor-MDP are double the concentration that these components will have in the final emulsion. In order to prepare the immunogens used in Example 4, the conjugate was dissolved in phosphate buffered saline ("PBS"), pH=7.2, to a concentration of 8.0 mg/ml. Nor-MDP adjuvant was dissolved in PBS to a concentration of 0.4 mg/ml. These two PBS solutions were then mixed together in a 1:1 ratio (vol:vol), yielding an aqueous phase solution containing 4.0 mg/ml. conjugate and 0.2 mg/m. nor-MDP.

The aqueous phase was combined 1:1 (vol:vol) with the oily vehicle phase to create an emulsion that comprised the final immunogen formulation. Various types of oily vehicles, known to those skilled in the art, may be used. One such vehicle is a mixture of four parts squalene and one part arlacel. The preferred oily vehicle for use with the immunogens of the invention is stabilized Montanide ISA 703 produced by Seppic (Paris, France). Montanide ISA 703 is not satisfactory for use alone and must have a stabilizing component added to it so that it can be used in the emulsion. The aqueous phase and oily phase vehicle can be mixed by any method known to those skilled in the art to form a stable emulsified mixture. The emulsion must be stable upon storage (e.g., not undergo a significant degree of separation into aqueous and vehicle phases for a minimal storage time of several weeks) and it must be of a consistency that allows it to be easily injected through an acceptable size hypodermic needle.

To stabilize Montanide ISA 703 oily vehicle we added aluminum monostearate ("AMS"). To determine the correct concentration of AMS, various concentrations of AMS were tested with the Montanide ISA 703 vehicle. The AMS was USP/NF Grade, #AL228, from Spectrum Chemical Manufacturing Corp. (Gardena, Calif., U.S.A.). Samples of Montanide ISA 703 were tested to which the following percent concentrations of AMS were added: 0; 0.8; 1.0; 1.2; 1.4; 1.6; 1.8; 2.0; 2.4; and 2.8%. Emulsions were made with an aqueous phase containing 4.0 mg/ml of conjugate and 0.5 mg/ml of nor-MDP adjuvant as described below with each sample vehicle preparation and assessed for stability and viscosity. An AMS range from about 1.5% to about 20% W/W was found to be acceptable. Montanide ISA 703 containing 1.6% and 1.8% AMS produced satisfactory emulsions, with 1.8% AMS being preferable. The sample vehicle preparations containing percent concentrations of 2.0% AMS and above produced emulsions that were too viscous and the sample vehicle containing 1.4% or less AMS produced unstable emulsions or totally failed to emulsify. The vehicle used in this application for administering the immunogens was Montanide ISA 703 containing 1.8% AMS, and is referred to as "Montanide ISA 703 AMS."

The aqueous phase containing the immunogen was emulsified 1:1 (vol:vol) with the Montanide ISA 703 AMS vehicle phase by pressing a mixture of the two solutions through an 18 gauge double hubbed needle between two glass syringes. The mixture was pressed through the needle 40 times. The emulsified mixture was then drawn into disposable syringes for injection into animals. The final concentrations in the emulsion of the immunogens used in Example 4 were: conjugate=hG17(1- 9)Ser9-DT:2.0 mg/ml.; nor-MDP adjuvant:0.25mg/ml. The concentration of AMS in the oily vehicle was 1.8% which resulted in 0.9% AMS in the final mixed emulsion.

Example 3

We constructed conjugates comprising each of the peptides listed in Example 1 linked to DT, as described in Example 1 and 2. We then immunized rabbits. Ten Rabbits were immunized with the Peptide 1 immunogen, and four rabbits with the Peptide 2 immunogen. We additionally immunized four rabbits with hG17(1-6)-Arg6 linked to DT as set forth in U.S. Pat. No. 5,023,077. The conjugates were administered in emulsions prepared as in Example 2, except that the oily vehicle phase consisted of a squalene:arlacel solution (comprising 4 parts squalene to 1 part arlacel) and the final concentrations of conjugate were 1.0 mg/ml and adjuvant were 0.2 mg/ml in each emulsion. A 0.5 ml. aliquot of the emulsion was injected into each rabbit. Each rabbit was given immunizations on days 0, 21 and 42 of the tests with 0.5 mg of conjugate injected intramuscularly per dose. Blood was collected from each rabbit prior to the first injection (day 0) and on days 14,35,56 and 84. Serum was prepared from each blood sample and stored at −20° C. until utilized in assays to determine the presence of anti-gastrin antibodies. Anti-hG17 antibody levels were determined by RIA.

A liquid phase Radioimmunoassay (RIA) was used to detect and quantify anti-gastrin antibodies. In the RIA, 1.0 or 10.0 μl aliquots of antiserum were incubated with approximately 250 pg of $^{125}I$ labeled hG17 (specific activity=18 Ci/m mole) total volume of 400 μl. Dilutions were made in FTA Hemagglutination Buffer (BBL, Becton Dickinson Microbiology Systems, Md., U.S.A.) containing 1% bovine serum albumin. The antisera were incubated with labeled hormone overnight at 4° C. Following this incubation, 0.1 ml of heat inactivated (56° c., 30 rain) fetal calf serum at 4° C. was then added to each tube. The antibody-hormone complexes were then precipitated by the addition of 0.1 ml of 25% polyethylene glycol (MW=8,000 gin/mole) at 4° C. The precipitates were pelleted by centrifugation (30 minutes at 1000×g), the supernatants were discarded, and the pellets were counted with a gamma counter to measure the quantity of radioactivity contained therein. Antigen binding capacities (ABC) for each antiserum were then determined from the amount of radioactive hormone in the precipitate. Serum taken from the rabbits prior to immunization served as nonimmunized (normal) controls. Nonspecific background binding was subtracted from all values. To demonstrate the specificity of the reaction of $^{125}I$ labeled hormone with the antisera, aliquots of the antisera were preincubated in some tests with excess amounts of hG17 that was not labeled with $^{125}I$, to inhibit binding of the antisera to the labeled hormone.

The results of this test are presented in Table 1 and in FIG. 1. As can be seen therein, Immunogens 1 and 2 (of Example 1) were superior to Immunogen 3, in terms of both the potency and the duration of the anti-hG17 antibody responses induced by the immunogens.

The improvements to the immunogen arise from modifications made to the immunomimic and spacer regions of the peptide. The peptides that comprise Immunogens 2 and 3 have identical Arg spacers, but Immunogen 2 is considerably more potent because its peptide has an improved immunomimic of hG17 (for day 84, p=0.05, Student's t tests. Conversely, the peptides that comprise Immunogens 1 and 2 incorporate the same immunomimic of hG17; yet, Immunogen 1 is more immunogenic because it possesses a superior spacer element (the Ser spacer) (for day 84, p=0.001). The immunogens thus can be improved by modifying the spacer and/or the immunomimic.

TABLE 1

RABBIT SERUM ANTI-hG17 ANTIBODY LEVELS
INDUCED BY ANTI-hG17 IMMUNOGENS
ADMINISTERED ON DAYS 0, 21 AND 42

| IMMUNOGEN NUMBER | PEPTIDE DESIGNATION | MEAN RIA ABC (± s.e.) [pmole/ml] | | | | |
|---|---|---|---|---|---|---|
| | | Day 0 | Day 14 | Day 35 | Day 56 | Day 84 |
| 1 | hG17(1-9)-Ser9 | 0 | 1 ± 1 | 31 ± 4 | 117 ± 6 | 170 ± 8 |
| 2 | hG17(1-9)-Arg9 | 0 | 1 ± 1 | 25 ± 7 | 98 ± 22 | 76 ± 18 |
| 3 | hG17(1-6)-Arg6 | 0 | 0 | 10 ± 2 | 23 ± 2 | 11 ± 3 |

Example 4

Six female rabbits were immunized with the hG17(1-9)Ser9-DT conjugate produced by the methods of Example 1 and 2 by intramuscular administration. The immunogen comprised 2.0 mg/ml hG17(1-9)Ser9-DT conjugate and 0.25 mg/ml nor-MDP adjuvant in PBS emulsified with Montanide ISA 703 AMS. Each rabbit was injected only on day 0 of the test. The volume injected was 1.0 ml. per rabbit. Every 7 days thereafter, blood samples were obtained from each rabbit. Serum was prepared from each blood sample and stored at −20° c., until utilized in assays to determine the presence of anti-gastrin antibodies.

Figure 2:
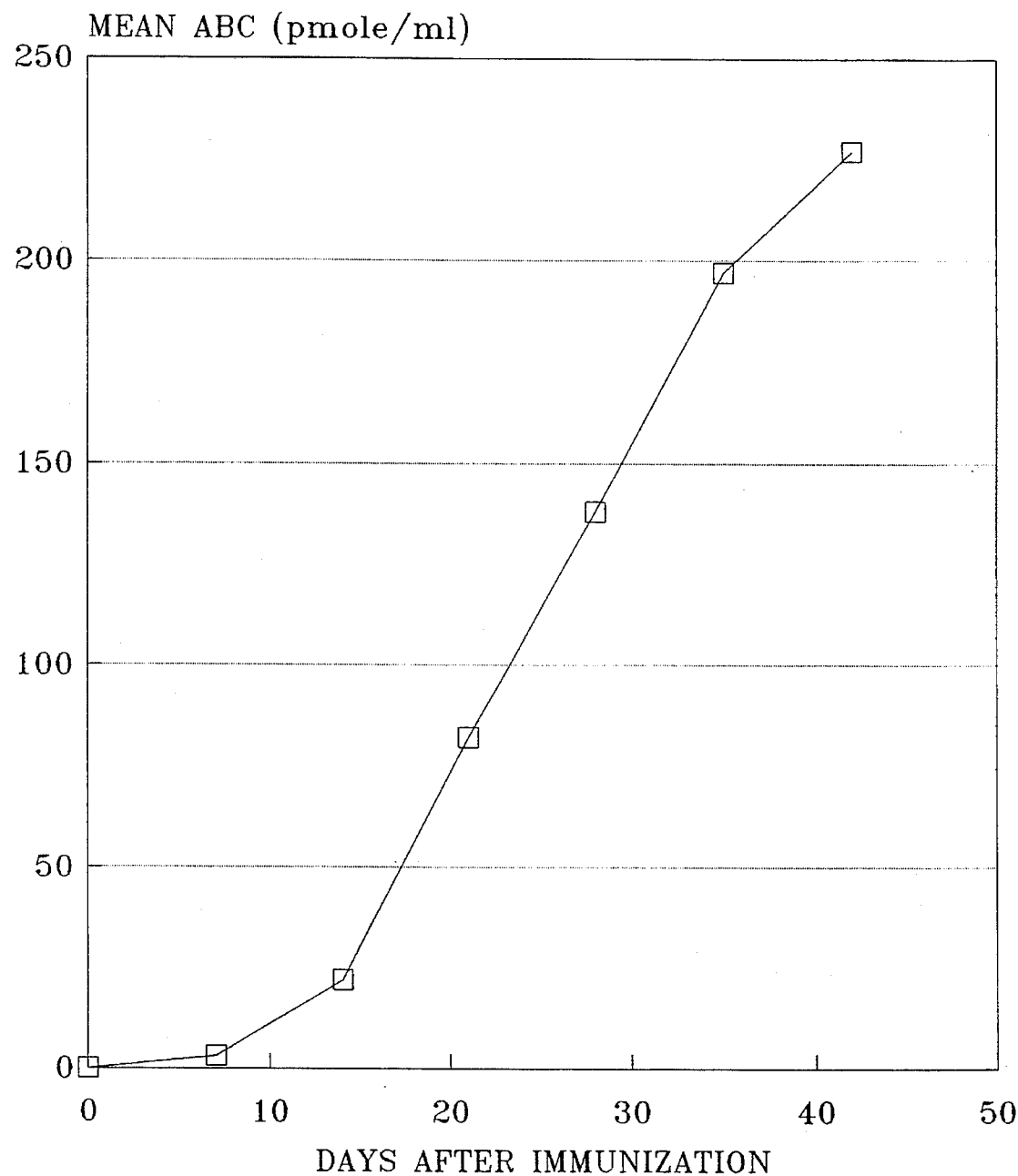
FIG. 2 depicts the antibody response in rabbits as measured by mean antibody binding capacity ("ABC") in pico moles per ml immunized with one administration of a conjugate constructed with peptide 1 (hG17(1-9)-Ser9-DT) of Example 1.

The mean ABCs measured in the sera from rabbits immunized with the immunogens of Example 1 are shown in Table 2 and in FIG. 2. As these results show, a single administration of immunogen induced a rapid and potent antibody response against hG17. 42 days after the immunogen was injected, a mean antibody level of 227 pmoles of hG17 bound per ml of antiserum had been induced in the rabbits. As can be seen in FIG. 2, the anti-hG17 antibody response was still increasing at a rapid rate on day 42.

TABLE 2

RABBIT SERUM ANTI-hG17 ANTIBODY LEVELS INDUCED BY IMMUNIZATION ON DAY 0 OF THE TEST
Mean RIA ABC (± s.e.) [pmole/ml]

| Day of Test | 0 | 7   | 14   | 21   | 28    | 35    | 42    |
|-------------|---|-----|------|------|-------|-------|-------|
| ABC         | 0 | 3 ± | 22 ± | 82 ± | 138 ± | 197 ± | 227 ± |
|             |   | 1   | 6    | 20   | 27    | 30    | 25    |

We claim:

1. A immunogenic composition comprising the peptide pGlu-Gly-Pro-Trp-Leu-Glu-Glu-Glu-Glu-Ser-Ser-Pro-Pro-Pro-Pro-Cys SEQ ID NO.: 1, coupled to an immunogenic carrier.

2. The immunogenic composition of claim 1 wherein the immunogenic carrier is selected from the group consisting of diphtheria toxoid, tetanus toxoid and keyhole limpet hemocyanin.

3. The immunogenic composition of claim 2 wherein the immunogenic carrier is diphtheria toxoid.

4. A pharmaceutical composition comprising an effective amount of the immunogenic composition of claims 1, 2 or 3 and a pharmaceutically acceptable carrier.

5. The pharmaceutical composition of claim 4 wherein the pharmaceutically acceptable carrier comprises an emulsion of an aqueous phase and an oily phase, wherein the oily phase is an oily vehicle comprising Montanide ISA 703 containing from about 1.5% W/W to about 2.0% W/W aluminum monostearate.

6. The peptide pGlu-Gly-Pro-Trp-Leu-Glu-Glu-Glu-Glu-Ser-Ser-Pro-Pro-Pro-Pro-Cys, SEQ ID NO.: 1.

7. The spacer peptide Ser-Ser-Pro-Pro-Pro-Pro-Cys, SEQ ID NO.: 3.

* * * * *

UNITED STATES PATENT AND TRADEMARK OFFICE
CERTIFICATE OF CORRECTION

PATENT NO.   : 5,468,494
DATED        : November 21, 1995
INVENTOR(S)  : Philip C. Gevas, Stephen Grimes, Stephen L. Karr, Dov Michaeli, and Robert Scibienski It is certified that error appears in the above-indentified patent and that said Letters Patent is hereby corrected as shown below:

In column 9, lines 48 and 52, change "carder" to -- carrier --.

Signed and Sealed this

Twenty-ninth Day of October 1996

Attest:

BRUCE LEHMAN

*Attesting Officer*   *Commissioner of Patents and Trademarks*